United States Patent
McCawley

(10) Patent No.: US 9,060,841 B2
(45) Date of Patent: Jun. 23, 2015

(54) ENHANCED FLOW VITRECTOMY PROBE

(75) Inventor: Matthew Douglas McCawley, San Clemente, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 458 days.

(21) Appl. No.: 13/222,060

(22) Filed: Aug. 31, 2011

(65) Prior Publication Data

US 2013/0053759 A1  Feb. 28, 2013

(51) Int. Cl.
*A61B 17/32* (2006.01)
*A61F 9/007* (2006.01)
*A61B 17/3207* (2006.01)

(52) U.S. Cl.
CPC ....... *A61F 9/00763* (2013.01); *A61B 17/32002* (2013.01); *A61B 17/320783* (2013.01)

(58) Field of Classification Search
CPC ............ A61F 9/00736; A61F 9/00745; A61F 9/00763; A61B 17/320783; A61B 17/32002; A61B 2017/320024; A61B 2017/320028; A61B 2017/320084; A61B 2017/00544
USPC ...................... 604/22; 606/107, 166, 170, 171
See application file for complete search history.

(56) References Cited

U.S. PATENT DOCUMENTS

| | | |
|---|---|---|
| 812,162 A | 2/1906 | Bemis |
| 2,016,746 A | 10/1935 | Ireland |
| 2,707,389 A | 5/1955 | Fortier |
| 3,084,674 A | 4/1963 | Watson |
| 3,477,665 A | 11/1969 | Legrand |
| 3,646,727 A | 3/1972 | Wachsmuth |
| 3,703,139 A | 11/1972 | Furlong |
| 3,815,604 A | 6/1974 | O'Malley et al. |
| 3,854,382 A | 12/1974 | Walters et al. |
| 3,867,934 A | 2/1975 | Ollivier |
| 4,011,869 A | 3/1977 | Seiler, Jr. |
| 4,077,567 A | 3/1978 | Ginn et al. |
| 4,086,804 A | 5/1978 | Ruby |
| 4,164,167 A | 8/1979 | Imai et al. |
| 4,168,707 A | 9/1979 | Douvas et al. |
| 4,253,480 A | 3/1981 | Kessel et al. |

(Continued)

FOREIGN PATENT DOCUMENTS

| | | |
|---|---|---|
| DE | 37 08 989 | 10/1988 |
| DE | 3925405 A1 | 2/1991 |

(Continued)

OTHER PUBLICATIONS

International Searching Authority, International Search Report, PCT/US2012/049695, Oct. 24, 2012, 2 pages.

(Continued)

*Primary Examiner* — Kathleen Holwerda
*Assistant Examiner* — Sarah W Aleman

(57) ABSTRACT

An enhanced flow ophthalmic surgical probe for ophthalmic microsurgery, such as vitrectomy, in an eye of a patient is disclosed. The enhanced flow probe includes a body, a needle, a cutter, and an optional stiffening sleeve. The needle, the cutter, and the optional stiffening sleeve each possess a widened diameter at its proximal portion relative to the diameter at its distal portion, thereby providing an enhanced ophthalmic surgical probe that allows adequate stiffness, reduced flow resistance, and an increased flow rate while maintaining a less invasive, large gauge diameter needle and cutter.

15 Claims, 3 Drawing Sheets

(56) References Cited

U.S. PATENT DOCUMENTS

| | | |
|---|---|---|
| 4,323,064 A | 4/1982 | Hoenig et al. |
| 4,331,130 A | 5/1982 | Lewicky |
| 4,335,867 A | 6/1982 | Bihlmaier |
| 4,344,144 A | 8/1982 | Damico et al. |
| 4,368,734 A | 1/1983 | Banko |
| 4,476,532 A | 10/1984 | Akiyama et al. |
| 4,590,935 A | 5/1986 | Ranalli |
| 4,622,503 A | 11/1986 | Sundblom et al. |
| 4,650,460 A | 3/1987 | Roizenblatt |
| 4,650,462 A | 3/1987 | DeSatnick et al. |
| 4,678,459 A | 7/1987 | Onik et al. |
| 4,679,583 A | 7/1987 | Lucas et al. |
| 4,696,298 A | 9/1987 | Higgins et al. |
| 4,706,687 A | 11/1987 | Rogers et al. |
| 4,757,814 A | 7/1988 | Wang et al. |
| 4,770,654 A | 9/1988 | Rogers et al. |
| 4,790,816 A | 12/1988 | Sundblom et al. |
| 4,810,242 A | 3/1989 | Sundblom et al. |
| 4,840,111 A | 6/1989 | Garnjost |
| 4,933,843 A | 6/1990 | Scheller et al. |
| 4,985,027 A | 1/1991 | Dressel |
| 5,019,035 A | 5/1991 | Missirlian et al. |
| 5,020,315 A | 6/1991 | Leachman, Jr. et al. |
| 5,020,825 A | 6/1991 | Lizell |
| 5,024,654 A | 6/1991 | Tyler |
| 5,047,008 A * | 9/1991 | de Juan et al. ............... 604/22 |
| 5,092,178 A | 3/1992 | Vanderlaan |
| 5,094,260 A | 3/1992 | Stuart et al. |
| 5,106,364 A | 4/1992 | Hayafuji et al. |
| 5,138,564 A | 8/1992 | de Jong et al. |
| 5,154,207 A | 10/1992 | Bolt |
| 5,176,628 A | 1/1993 | Charles et al. |
| 5,217,465 A | 6/1993 | Steppe |
| 5,239,861 A | 8/1993 | Fujita et al. |
| 5,314,295 A | 5/1994 | Lukkari et al. |
| 5,380,280 A | 1/1995 | Peterson |
| 5,403,276 A | 4/1995 | Schechter et al. |
| 5,417,246 A | 5/1995 | Perkins et al. |
| 5,437,241 A | 8/1995 | Rosenberg et al. |
| 5,445,773 A | 8/1995 | Arai |
| 5,457,625 A | 10/1995 | Lim et al. |
| 5,549,139 A | 8/1996 | Perkins et al. |
| 5,550,685 A | 8/1996 | Drouin |
| 5,571,248 A | 11/1996 | Seetharaman et al. |
| 5,580,347 A | 12/1996 | Reimels |
| 5,587,536 A | 12/1996 | Rasmussen |
| 5,630,827 A | 5/1997 | Vijfvinkel |
| 5,674,194 A | 10/1997 | Jung et al. |
| 5,791,142 A | 8/1998 | Layne et al. |
| 5,808,396 A | 9/1998 | Boukhny |
| 5,810,765 A | 9/1998 | Oda |
| 5,829,335 A | 11/1998 | Ewald et al. |
| 5,846,257 A | 12/1998 | Hood |
| 5,857,485 A | 1/1999 | Perkins et al. |
| 5,959,390 A | 9/1999 | Boukhny |
| 5,979,494 A | 11/1999 | Perkins et al. |
| 5,989,262 A | 11/1999 | Josephberg |
| 5,993,409 A * | 11/1999 | Maaskamp ............... 604/22 |
| 6,155,233 A | 12/2000 | Wade et al. |
| 6,162,187 A | 12/2000 | Buzzard et al. |
| 6,423,074 B1 * | 7/2002 | Chen ............... 606/107 |
| 6,425,883 B1 | 7/2002 | Urich et al. |
| 6,450,966 B1 | 9/2002 | Hanna |
| 6,485,436 B1 | 11/2002 | Truckai et al. |
| 6,514,268 B2 | 2/2003 | Finlay et al. |
| 6,527,736 B1 | 3/2003 | Attinger et al. |
| 6,575,264 B2 | 6/2003 | Spadafora |
| 6,575,990 B1 | 6/2003 | Wang et al. |
| 6,678,584 B2 | 1/2004 | Junk et al. |
| 6,730,106 B2 | 5/2004 | Kanda et al. |
| 6,773,445 B2 | 8/2004 | Finlay et al. |
| 6,779,541 B2 | 8/2004 | Inayama et al. |
| 6,848,323 B2 | 2/2005 | Krouth et al. |
| 6,851,453 B2 | 2/2005 | Lipscomb et al. |
| 6,892,745 B2 | 5/2005 | Benson |
| 6,954,683 B2 | 10/2005 | Junk et al. |
| 6,999,853 B2 | 2/2006 | Junk et al. |
| 7,244,240 B2 | 7/2007 | Nazarifar et al. |
| 7,263,877 B2 | 9/2007 | Schaefer et al. |
| 7,283,321 B1 | 10/2007 | Sun et al. |
| 7,335,217 B2 | 2/2008 | Wang et al. |
| 7,337,041 B2 | 2/2008 | Junk et al. |
| 7,352,287 B2 | 4/2008 | Rupert |
| 7,470,277 B2 | 12/2008 | Finlay et al. |
| 7,600,405 B2 | 10/2009 | Maurer, Jr. et al. |
| 7,628,054 B2 | 12/2009 | Hajishah et al. |
| 7,640,119 B2 | 12/2009 | Khashayar |
| 7,708,734 B2 | 5/2010 | Khashayar |
| 7,775,052 B2 | 8/2010 | Cornwell et al. |
| 8,038,692 B2 | 10/2011 | Valencia et al. |
| 8,157,145 B2 | 4/2012 | Shelton, IV et al. |
| 8,187,293 B2 | 5/2012 | Kirchhevel |
| 8,202,277 B2 | 6/2012 | Ryan |
| 8,215,108 B2 | 7/2012 | Hahn et al. |
| 8,230,877 B2 | 7/2012 | Roberge et al. |
| 8,308,737 B2 | 11/2012 | Ryan |
| 2002/0117214 A1 | 8/2002 | Tucker et al. |
| 2003/0042182 A1 | 3/2003 | Moscaritolo |
| 2003/0195538 A1 | 10/2003 | Wang et al. |
| 2003/0208305 A1 | 11/2003 | Junk et al. |
| 2004/0154466 A1 | 8/2004 | Gethmann et al. |
| 2004/0186484 A1 | 9/2004 | Ryan |
| 2005/0033309 A1 | 2/2005 | Ryan |
| 2005/0245909 A1 | 11/2005 | McCary et al. |
| 2006/0129062 A1 | 6/2006 | Nicoson et al. |
| 2006/0271082 A1 | 11/2006 | Kirchevel et al. |
| 2007/0093793 A1 | 4/2007 | Maurer, Jr. et al. |
| 2007/0185512 A1 | 8/2007 | Kirchhevel |
| 2007/0219647 A1 | 9/2007 | Heertjes et al. |
| 2007/0270735 A1 | 11/2007 | Williams et al. |
| 2007/0270746 A1 | 11/2007 | King |
| 2007/0282262 A1 | 12/2007 | Williams et al. |
| 2008/0082077 A1 | 4/2008 | Williams |
| 2008/0103433 A1 | 5/2008 | Nazarifar et al. |
| 2008/0108980 A1 | 5/2008 | Turner et al. |
| 2008/0110236 A1 | 5/2008 | Hajishah et al. |
| 2008/0142093 A1 | 6/2008 | Turner et al. |
| 2008/0146988 A1 | 6/2008 | Olivera et al. |
| 2008/0149197 A1 | 6/2008 | Turner et al. |
| 2008/0168985 A1 | 7/2008 | Turner et al. |
| 2008/0172077 A1 * | 7/2008 | Valencia et al. ............... 606/170 |
| 2008/0172078 A1 | 7/2008 | Svetic |
| 2008/0300580 A1 | 12/2008 | Shelton, IV et al. |
| 2009/0082715 A1 | 3/2009 | Charles et al. |
| 2009/0124962 A1 | 5/2009 | Hopkins et al. |
| 2009/0203480 A1 | 8/2009 | Petzold et al. |
| 2009/0259242 A1 | 10/2009 | Gerg et al. |
| 2009/0287233 A1 | 11/2009 | Huculak |
| 2009/0305214 A1 | 12/2009 | Pybus et al. |
| 2010/0145374 A1 | 6/2010 | Perkins et al. |
| 2010/0305596 A1 | 12/2010 | Peterson et al. |
| 2010/0312169 A1 | 12/2010 | Auld et al. |
| 2011/0005387 A1 | 1/2011 | Ehre et al. |
| 2011/0054508 A1 | 3/2011 | Zhou et al. |
| 2011/0144675 A1 | 6/2011 | Gao et al. |
| 2011/0295293 A1 | 12/2011 | Agahi |
| 2011/0299943 A1 | 12/2011 | Woolever |
| 2012/0010602 A1 | 1/2012 | Ryan |
| 2012/0055329 A1 | 3/2012 | Heer |
| 2012/0157906 A1 | 6/2012 | Underwood |
| 2012/0157907 A1 | 6/2012 | Underwood |
| 2012/0157908 A1 | 6/2012 | Underwood |
| 2012/0157909 A1 | 6/2012 | Underwood |
| 2012/0158006 A1 | 6/2012 | McDonell |
| 2012/0158029 A1 | 6/2012 | Underwood |
| 2012/0158030 A1 | 6/2012 | Underwood |
| 2012/0221033 A1 | 8/2012 | Auld |

FOREIGN PATENT DOCUMENTS

| | | |
|---|---|---|
| DE | 4232586 A1 | 3/1994 |
| DE | 19821420 C1 | 10/1999 |
| DE | 10247869 A1 | 5/2004 |
| DE | 202005009670 U1 | 9/2005 |

(56) References Cited

FOREIGN PATENT DOCUMENTS

| | | |
|---|---|---|
| DE | 10247869 B4 | 2/2007 |
| DE | 102006030034 | 1/2008 |
| EP | 0469641 B1 | 6/1989 |
| EP | 0626628 A1 | 11/1994 |
| EP | 0673475 B1 | 6/1996 |
| EP | 0626628 B1 | 12/1997 |
| EP | 0874163 A2 | 10/1998 |
| EP | 0884667 A1 | 12/1998 |
| EP | 0874163 A3 | 3/1999 |
| EP | 1074271 A2 | 2/2001 |
| EP | 1074271 A3 | 2/2002 |
| EP | 1172586 B1 | 3/2004 |
| EP | 1074271 B1 | 10/2004 |
| EP | 1660244 B1 | 12/2006 |
| EP | 2032878 B1 | 12/2009 |
| GB | 792397 A | 3/1958 |
| GB | 1189493 A | 6/1970 |
| GB | 1213723 A | 11/1970 |
| GB | 1 323 788 A | 7/1973 |
| GB | 1417299 | 12/1975 |
| GB | 2016746 A | 9/1979 |
| GB | 2 140 871 A | 12/1984 |
| GB | 2203195 A | 10/1988 |
| GB | 2389423 A | 12/2003 |
| JP | 07259801 A | 10/1995 |
| JP | 09225698 A | 9/1997 |
| JP | 9311091 A | 12/1997 |
| JP | 2010-057642 | 3/2010 |
| WO | 92/02866 A1 | 2/1992 |
| WO | 93/18445 A1 | 9/1993 |
| WO | WO 95/31141 A1 | 11/1995 |
| WO | WO 00/78371 A1 | 12/2000 |
| WO | WO 01/30281 A1 | 5/2001 |
| WO | WO 01/64120 A1 | 9/2001 |
| WO | WO 2008/000599 A1 | 1/2008 |
| WO | 2008/029066 A1 | 3/2008 |
| WO | WO 2008/054944 A1 | 5/2008 |
| WO | WO 2008/079526 A2 | 7/2008 |
| WO | WO 2008/079526 A3 | 8/2008 |
| WO | WO 2008/105950 A2 | 9/2008 |
| WO | WO 2008/140537 A1 | 11/2008 |
| WO | WO 2008/147429 A2 | 12/2008 |
| WO | WO 2008/147429 A3 | 3/2009 |
| WO | WO 2008/105950 A3 | 9/2009 |
| WO | WO 2010/066302 A1 | 6/2010 |
| WO | WO 2011/025658 A1 | 3/2011 |
| WO | 2011/071613 A1 | 6/2011 |
| WO | WO 2011/071655 A1 | 6/2011 |
| WO | 2011/138102 A1 | 11/2011 |
| WO | 2011/149621 A1 | 12/2011 |
| WO | 2013/032633 A1 | 3/2013 |

OTHER PUBLICATIONS

International Searching Authority, Written Opinion of the International Searching Authority, PCT/2012/049695, Oct. 24, 2012, 4 pages.
Underwood, John R., Vitrectomy Probe with Adjustable Cutter Port Size, U.S. Appl. No. 12/974,722, filed Dec. 21, 2010, 55 pages.
Auld, Jack Robert, Surgical Probe with Increased Fluid Flow, U.S. Appl. No. 13/036,401, filed Feb. 28, 2011, 20 pages.
McDonell, Brian William, Reduced Friction Vitrectomy Probe, U.S. Appl. No. 13/304,792, filed Nov. 28, 2011, 24 pages.
McDonell, Brian W., Optimized Pneumatic Drive Lines, U.S. Appl. No. 13/314,625, filed Dec. 8, 2011, 32 pages.
Underwood, John R., Vitrectomy Probe with Adjustable Cutter Port Size, U.S. Appl. No. 12/974,740, filed Dec. 21, 2010, 54 pages.
Underwood, John R., Vitrectomy Probe with Adjustable Cutter Port Size, U.S. Appl. No. 13/219,089, filed Aug. 26, 2011, 54 pages.
Underwood, John R., Vitrectomy Probe with Adjustable Cutter Port Size, U.S. Appl. No. 13/218,923, 51 pages.
Underwood, John R., Vitrectomy Probe with Adjustable Cutter Port Size, U.S. Appl. No. 13/219,017, 57 pages.
Underwood, John R., Vitrectomy Probe with Adjustable Cutter Port Size, U.S. Appl. No. 13/218,826, 55 pages.
Kabei, Shimemura, et al., A portable pneumatic driving unit for a left ventricular assist device, Int. J. Artif. Organs, 1988, 186-90, 11(3).
Nachlas, Marvin, et al., A simple portable pneumatic pump for external cardiac massage, The American Journal of Cardiology, 1962, 107-109, 10(1).
Waldeck, J.L., The development of a portable pressure source for the static and dynamic calibration of pressure transducers, The Journal of Wind Engineering and Industrial Aerodynamics, 1987, 213-230, 26(2).
Ellis, George, et al., Microcomputer-Controlled Precision Pressure Generator, IEEE Transactions on Instrumentation and Measurement, 1977, 214-217, 26(3).
Whalen, R.L., et al., An electromagnetic pneumatic blood pump driver, American Society of Artificial Internal Organs, 1988, 721-725, 34(3).
Turkentine, R.B., et al., Pressure-operated shutter for thin-film monitor, Journal of Physics E: Scientific Instruments, 1979, 12(1).
Rogers, Richard C., An inexpensive picoliter-volume pressure ejection system, Brain Research Bulletin, 1985, 669-671, 15(6).
Johnson, Kenneth S., et al., A submersible flow analysis System, Analytical Chimica Acta, 1986, 245-257, 179.
Tabassum, Alim Abid, Solar refrigeration: evaluation of technical options and design of a solar-generator-adsorber for a novel adsorption refrigerator, Tabassum thesis, Cranfield University, 1989.
Buchanan, P.R., et al., Recovery of ventilation distributions by gas wash-out of a mechanical pump, Clinical Physics and Physiological Measurement, 1986, 7(3).
Agahi, Daryush, "Feedback of On/Off Pneumatic Actuators," U.S. Appl. No. 12/788,609, filed May 27, 2010, 24 pgs.
Zhou, Jason, et al., "Pneumatic Pressure Output Control by Drive Valve Duty Cycle Calibration," U.S. Appl. No. 12/854,281, filed Aug. 11, 2010, 38 pgs.
International Searching Authority, International Search Report, PCT/US2010/056305, Mar. 2, 2011, 3 pages.
International Searching Authority, Written Opinion of the International Searching Authority, PCT/US2010/056305, Mar. 2, 2011, 7 pages.
International Searching Authority, International Search Report, PCT/US2010/045136, Nov. 18, 2010, 4 pages.
International Searching Authority, Written Opinion of the International Searching Authority, PCT/US2010/045136, Nov. 18, 2010, 6 pages.
International Searching Authority, International Search Report, PCT/US2011/034720, Jul. 28, 2011, 2 pages.
International Searching Authority, Written Opinion of the International Searching Authority, PCT/US2011/034720, Jul. 20, 2011, 8 pages.
Nguyen, Tuan Van, Non-Final Office Action, U.S. Appl. No. 12/944,039, Mar. 5, 2013, 29 pgs.
Nguyen, Tuan Van, Non-Final Office Action, U.S. Appl. No. 12/788,609, Jan. 18, 2012, 32 pages.
Nguyen, Tuan Van, Non-Final Office Action, U.S. Appl. No. 12/788,609, Jul. 12, 2012, 24 pages.

* cited by examiner

ENHANCED FLOW VITRECTOMY PROBE

BACKGROUND

The present disclosure relates generally to ophthalmic surgical probes. More particularly, but not by way of limitation, the present disclosure pertains to an enhanced flow vitrectomy probe.

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibrils that are often attached to the retina. Therefore, cutting and removal of the vitreous must be done with great care to avoid traction on the retina, the separation of the retina from the choroid, a retinal tear, or, in the worst case, cutting and removal of the retina itself. In particular, delicate operations such as mobile tissue management (e.g., cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. Such vitrectomy probes are typically inserted via an incision in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Standard commercially available vitrectomy probe shafts are of one gauge size (i.e., one constant diameter) from the proximal end to the distal end. U.S. Pat. No. 5,019,035 to Missirlian et al., U.S. Pat. No. 5,176,628 to Charles et al., and U.S. Patent Application No. US 2010/0312169 disclose various types of vitrectomy probes, and all of these patents are incorporated herein by reference. Current trends in posterior segment ophthalmic surgery are driving the development of ever smaller single shafted instrumentation to minimize trauma to the eye. However, as the probes become smaller and less invasive, the working diameter of the probes decreases, which negatively affects the ability of the probe to remove ocular tissue and/or fluid from the eye. As instrument gauge increases (i.e., the diameter decreases), the internal resistance to flow increases, thereby decreasing the rate of removal of ocular tissue and/or fluid from the eye. Moreover, as instrument gauge increases, the stiffness of the instrument decreases, thereby limiting the precise use of the instrument. Consequently, the adoption of smaller diameter instruments has been limited by, among other things, inadequate flow rates due to increased flow resistance and inadequate instrument stiffness.

Therefore, a need exists for an enhanced vitrectomy probe that allows adequate stiffness, reduced flow resistance, and an increased flow rate while maintaining a less invasive, smaller diameter shaft.

SUMMARY

This disclosure relates generally to, and encompasses, an apparatus and method for removing ocular tissue and/or fluid from the eye, and more specifically to an ophthalmic surgical probe and methods of using the device to remove ocular tissue and/or fluid from the eye.

In one exemplary embodiment, an ophthalmic surgical probe for insertion into the eye of a patient comprises a body, a hollow cutter, and a needle. The hollow cutter may include a first portion having a first diameter and a second portion having a second diameter sized smaller than the first diameter, wherein the first portion and the second portion are in fluid communication. The needle may include a third portion having a third diameter and a fourth portion having fourth diameter sized smaller than the third diameter, wherein the third portion and the fourth portion are in fluid communication. The cutter may be slidably disposed within the needle.

In another exemplary embodiment, an ophthalmic surgical probe for insertion into the eye of a patient comprises a body, a hollow cutter, a needle, and a hollow stiffening sleeve. The cutter may include a first portion having a first diameter and a second portion having a second diameter sized smaller than the first diameter, wherein the first portion and the second portion are in fluid communication. The needle may include a third portion having a third diameter and a fourth portion having fourth diameter sized smaller than the third diameter, wherein the third portion and the fourth portion are in fluid communication. The hollow stiffening sleeve may include a fifth portion having a fifth diameter and a sixth portion having sixth diameter sized smaller than the fifth diameter, wherein the third, fourth, fifth, and sixth portions are in fluid communication. The cutter may be slidably disposed within the needle and the stiffening sleeve. In some embodiments, the second portion may be configured to slide at least partially into the third portion and the fifth portion.

In another exemplary embodiment, a method for treating an eye of a patient comprises inserting a ophthalmic surgical probe into the eye, positioning the first portion of the hollow cutter and the third portion of the needle outside of the eye, and sliding the cutter within the needle. The probe may include a body, a hollow cutter, and a needle. The cutter may include a first portion having a first diameter and a second portion having a second diameter sized smaller than the first diameter, wherein the first portion and the second portion are in fluid communication. The needle may include a third portion having a third diameter and a fourth portion having fourth diameter smaller than the third diameter, wherein the third portion and the fourth portion are in fluid communication. In some embodiments, the ophthalmic surgical probe may further include a stiffening sleeve with a semi-rigid sheath disposed circumferentially around a segment of the needle.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
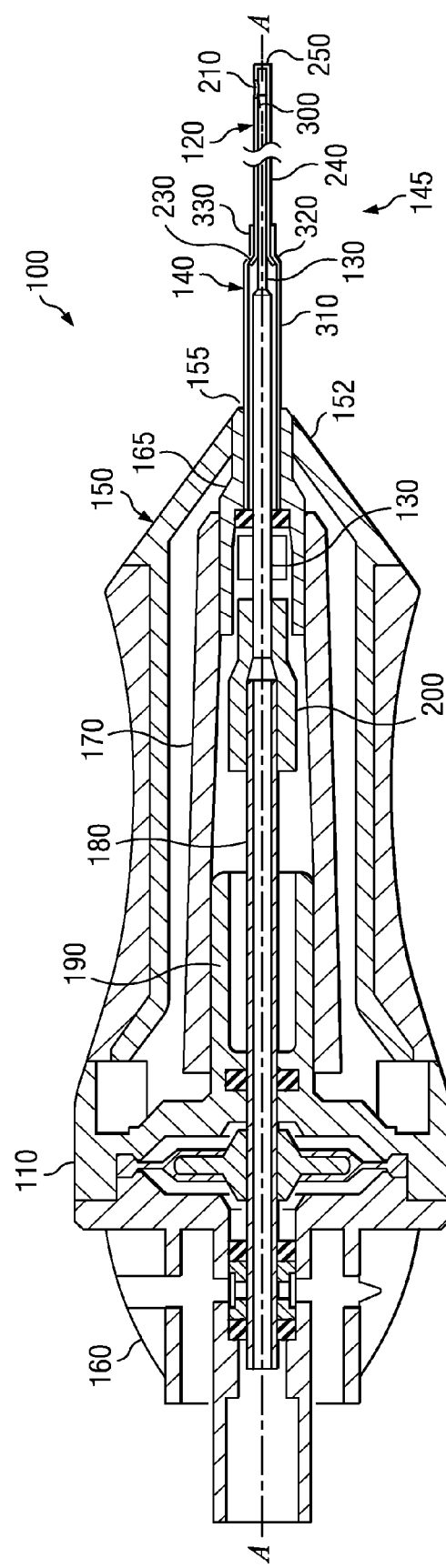
FIG. 1 is a cross-sectional view of an ophthalmic surgical probe according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to an apparatus, system, and method for removing ocular tissue and/or fluid from the eye. The various figures show embodiments of an ophthalmic surgical probe and methods of using the device to remove ocular tissue and/or fluid from a patient's eye. One of ordinary skill in the art, however, would understand that similar embodiments could be used to remove tissue and/or fluid from other locations in the body without departing from the general intent or teachings of the present disclosure.

FIG. 1 illustrates an ophthalmic surgical probe 100 according to an exemplary embodiment of the present disclosure for removing fluid/tissue from a patient's eye. The ophthalmic surgical probe 100 includes a body 110 coupled to a cannulated needle 120 by a stiffening sleeve 140. A cannulated cutter 130 extends through the needle 120 and the stiffening sleeve 140. The cutter 130, the needle 120, and the stiffening sleeve 140 cooperate to form an aspiration system 145. Although the ophthalmic surgical probe 100 according to an exemplary embodiment of the present disclosure is described herein in connection with a vitrectomy probe, the present disclosure is applicable to other ophthalmic or other surgical probes, instruments, and handpieces, each of which may include different component parts.

As shown in FIG. 1, the body 110 includes a housing 150 and an actuating assembly 160. The housing 150 has a proximal end 151 and a distal end 152. A generally central axis AA extends through the housing 150 through the proximal end 151 and the distal end 152. The housing 150 may be made of any suitable material, but is preferably made from a lightweight material such as aluminum or plastic.

An actuating assembly 160 may be connected to the proximal end 151 of the housing 150. In some embodiments, the actuating assembly 160 may be disposed within the housing 150. The actuating assembly 160 may be of any type of actuating assembly suitable for driving the ophthalmic surgical probe 100, such as a pneumatic actuating assembly or an electric motor.

The actuating assembly 160 is connected to a movable drive shaft 180 that extends along the axis AA through the housing 150. Within the housing 150, the drive shaft 180 may be supported for axial rotation and/or reciprocating motion by a drive shaft support member 190 that extends at least partially along a length of the drive shaft 180. The drive shaft 180 may be made of any suitable material, but is preferably made of stainless steel.

The housing 150 is coupled to the aspiration system 145. As mentioned above, the aspiration system 145 includes the stiffening sleeve 140, the needle 120, and the cutter 130. As shown in FIG. 1, the stiffening sleeve 140 extends at least partially within the housing 150 along the axis AA and through an opening 155 in the distal end 152 of the housing 150. A needle coupling 165 extends at least partially along the length of the stiffening sleeve 140 and supports the position of the stiffening sleeve 140 within the housing 150. The needle coupling 165 may be an integrally formed component of the housing 150 or of the stiffening sleeve 140. A needle holder 170 connects the needle coupling 165 to the drive shaft support member 190.

Figure 2:
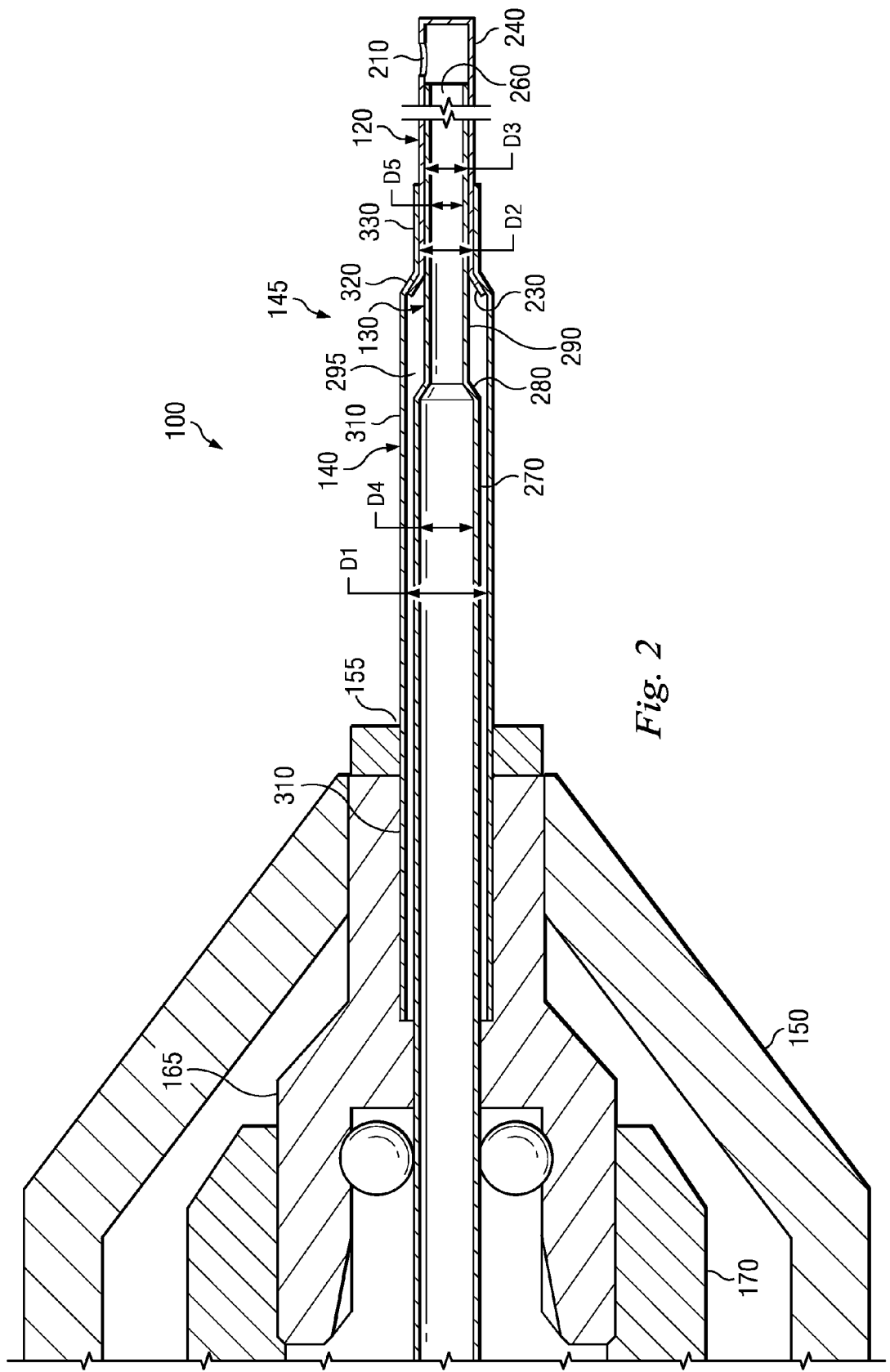
FIG. 2 is a cross-sectional view of a portion of the ophthalmic surgical probe according to the embodiment of FIG. 1.

As shown in FIGS. 1 and 2, the stiffening sleeve 140 is a hollow, rigid tube including a proximal portion 310, a connecting portion 320, and a distal portion 330. The stiffening sleeve 140 supports and stabilizes the needle 120 relative to the housing 150. The stiffening sleeve 140 may be sufficiently rigid as to prevent kinking or breaking the needle 120 during operation of the probe 100. The stiffening sleeve 140 is sized and configured to snugly surround a segment of the needle 120. The stiffening sleeve 140 may be integrally connected to the needle 120, or may be attached to the needle 120 using a variety of known methods, such as adhesive bonding, welding, lamination between two layers of polymers, or vapor deposition, for example. The needle coupling 165 may be integrally formed with the proximal end of the needle 120 and/or the stiffening sleeve 140.

As shown in FIG. 2, the connecting portion 320 is disposed between the proximal portion 310 and the distal portion 330. The proximal portion 310 of the stiffening sleeve 140 possesses a diameter D1 that is larger than the diameter D2 of the distal portion 330. The diameter of the stiffening sleeve 140 widens from the distal portion 330 to the proximal portion 310 to facilitate maximum aspiration and prevent plugging of ocular tissue and/or fluid in the probe 100. In this embodiment, the connecting portion 320 is a generally cone-shaped segment of the stiffening sleeve 140 that connects the proximal portion 310 to the distal portion 330 of the stiffening sleeve 140. In this embodiment, the connecting portion 320 includes a gradient of diameters ranging from the diameter D1 of the proximal portion 310 to the diameter D2 of the distal portion 330. In other embodiments, the connecting portion 320 may provide an abrupt shift in diameters between the proximal portion 310 and the distal portion 330. The stiffening sleeve 140 may be made of any suitable material, but is preferably made from surgical grade stainless steel.

As shown in FIG. 1, the needle 120 is a hollow, rigid, cylindrical tube that is coupled to the stiffening sleeve 140. The needle 120 is thin-walled along its entire length to allow maximum aspiration through the probe 100. The needle 120 is sized and configured to slidably contain the cutter 130 and to be slidably received within the connecting portion 320 and the distal portion 330 of stiffening sleeve 140.

As shown in greater detail in FIG. 2, the needle includes a connecting portion 230 and a distal portion 240. The distal portion 240 of the needle 120 possesses a diameter D3 that is smaller than the diameter D1 of the proximal portion 310 of the stiffening sleeve 140. The connecting portion 230 may be a generally cone-shaped segment of the needle 120 that fluidly connects the proximal portion 310 of the stiffening sleeve to the distal portion 240 of the needle 120. At the connecting portion 230 of the needle 120, the diameter of the needle 120 widens from the distal portion 240 to facilitate maximum aspiration and prevent plugging of ocular tissue and/or fluid in the probe 100. In this embodiment, the connecting portion 230 includes a gradient of diameters ranging from approximately the diameter D1 of the proximal portion 310 of the stiffening sleeve 140 to the diameter D3 of the distal portion 240 of the needle 120. In other embodiments, the connecting portion 230 may provide an abrupt shift in diameters between the proximal portion 310 and the distal portion 240. In some embodiments, the needle may lack a connecting portion. In such embodiments, the needle may possess a constant diameter and couple to the distal portion 330 of the stiffening sleeve 140.

An aperture 210 extends radially through a wall of the needle 120 in the distal portion 240. The aperture 210 is configured as a window that extends through the wall of the needle 120 in a direction perpendicular to the longitudinal axis of the needle 120. The aperture 210 is disposed near the distal end 250 of the needle 120. In this embodiment, the aperture 210 is generally circular and sized for a portion of the cutter 130 to operate therein. In other embodiments, the aperture 210 may have other shapes such as a square, an oval, or a rectangle. The edges of the aperture 210 may be beveled or sharpened to provide a cutting edge along the edge of the aperture 210.

The needle 120 may be made of any suitable material, but is preferably made from surgical grade stainless steel. For example, in the pictured embodiment, the distal portion of the needle 120 is a 25 gauge stainless steel tube.

In some embodiments, the stiffening sleeve may be an integral continuation of the needle such that the needle lacks a connecting portion of its own and includes the proximal and connecting portions of the stiffening sleeve 140.

As shown in FIG. 1, the cannulated cutter 130 is coupled to the drive shaft 180 by a cutter coupling 200, which extends at least partially along a distal end of the drive shaft 180 and at least partially along a distal end of the cutter 130. The cutter coupling 200 may be a sleeve, a clamp, a fitting, or any other mechanism known for linearly coupling components. Alternatively, the cutter coupling 200 may be integrally formed on the proximal end of the cutter 130. The cutter coupling 200 couples the drive shaft 180 to the cutter 130 such that the rotational and/or reciprocating motion of the drive shaft is transferred to the cutter 130. Thus, the cutter 130 may rotate about the axis AA or reciprocate along the axis AA in unison with the drive shaft 180. The cutter 130 extends within the stiffening sleeve 140 from within the housing 150 and out through the opening 155. The needle coupling 165 and the cutter coupling 200 may be made of any suitable material, but are preferably made from a lightweight material such as aluminum or plastic.

As shown in greater detail in FIG. 2, the cutter 130 is a hollow, rigid, cylindrical tube arranged coaxially within the needle 120 and the stiffening sleeve 140. The cutter 130 includes a lumen 260, a proximal portion 270, a connecting portion 280, and a distal portion 290. The connecting portion 280 is disposed between the proximal portion 270 and the distal portion 290. The cutter 130 is sized and configured to be slidably received and movably disposed within the needle 120 and the stiffening sleeve 140. In particular, the cutter 130 is sized such that the outer diameter of the cutter approaches the inner diameters of the needle 120 and stiffening sleeve 140, but the movement of the cutter 130 within the needle 120 and the stiffening sleeve 140 does not create undue friction against the inner wall of the needle 120 and the stiffening sleeve 140. The proximal portion 270 is at least partially disposed within the stiffening sleeve 140. The distal portion 290 of the cutter 130 extends through the distal portion 240 of the needle 120 into the proximal portion 310 of the stiffening sleeve 140. The proximal portion 270 of the cutter 130 possesses a diameter D4 that is larger than the diameter D5 of the distal portion 290. The diameter of the cutter 130 widens from the distal portion 290 to the proximal portion 270 to facilitate maximum aspiration and prevent plugging of ocular tissue and/or fluid in the lumen 260. In this embodiment, the connecting portion 280 is a generally cone-shaped segment of the cutter 130 that connects the proximal portion 270 to the distal portion 290 of the cutter 130. In this embodiment, the connecting portion 280 includes a gradient of diameters ranging from the diameter D4 of the proximal portion 270 to the diameter D5 of the distal portion 290. In other embodiments, the connecting portion 280 may provide an abrupt shift in diameters between the proximal portion 270 and the distal portion 290.

The cutter 130 may reside within the stiffening sleeve 140 such that a space 295 is formed between the outer surface of the connecting portion 280 and distal portion 290 of the cutter 130 and the inner surface the proximal portion 310 of the stiffening sleeve 140 and the connecting portion 230 of the needle 120. The space 295 is formed when the connecting portion 280 is retracted proximally from the connecting portion 230. During reciprocating motion of the cutter 130 within the needle 120, the volume of the space 295 decreases and increases. The connecting portion 230 of the needle 120, the connecting portion 320 of the stiffening sleeve 140, and the connecting portion 280 of the cutter 130 are sized and configured to prevent the proximal portion 270 of the cutter 130 from contacting or entering the distal portion 240 of the needle 120. The cutter 130 is thin-walled along its entire length to allow maximum aspiration through the lumen 260.

Referring back to FIG. 1, the cutter 130 includes a blade 300 that extends from the surface of the distal portion 290 of the cutter 130 in a direction substantially perpendicular to the longitudinal axis of the cutter 130. The blade 300 is sized and configured to operate within the aperture 210. In this embodiment, the blade 300 is generally flat with a beveled cutting edge. In other embodiments, the blade 300 may be any of a variety of shapes and configurations provided the blade 300 can operate to cut ocular tissue through the aperture 210. The blade 300 may be integrally formed with the cutter 130, or may be attached to the cutter 130 using a variety of known methods, such as adhesive bonding, lamination between two layers of polymers, or vapor deposition, for example. As will be explained in further detail below, moving the cutter 130 within and relative to the needle 120 causes the blade 300 to slide within the distal portion 240 of the needle 120 and across the aperture 210 such that ocular tissue is cut and aspirated into the lumen 260.

The cutter 130 and the blade 300 may be made of any suitable material, but are preferably made from surgical grade stainless steel. In some embodiments, the cutter is integrally formed of the proximal, connecting, and distal portions. In other embodiments, the distal portion is a separate component that cooperates with the integrally formed proximal and connecting portions to form the cutter.

Figure 3:
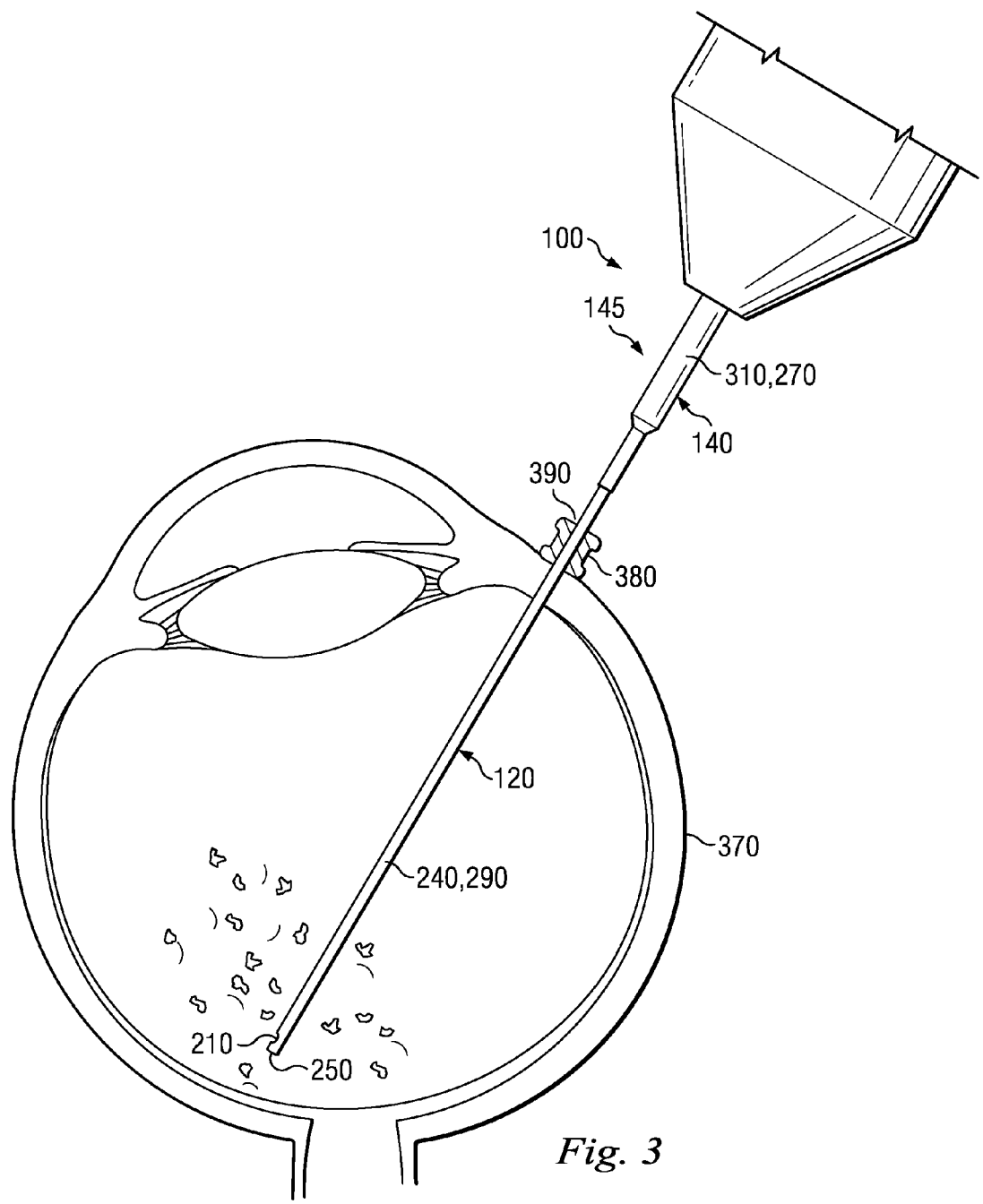
FIG. 3 is a view of an ophthalmic surgical probe according to one embodiment of the present disclosure shown inserted into an eye of a patient.

FIG. 3 illustrates the ophthalmic surgical probe 100 inserted into the eye 370 of a patient during an exemplary vitrectomy operation. Initially, the surgeon positions a cannula 380 at the surface of the eye 370 to establish a stable access port into the eye 370. The surgeon inserts the distal end 250 of the needle 210 through the cannula 380 into the posterior segment of the eye 370 using a pars plana insertion. The surgeon selects a desired vacuum level for a vacuum source. Ocular tissue and/or fluid is aspirated into the lumen 260 of the cutter 130 via the aperture 210 of the needle 120. In this example, the surgeon selects a desired cut rate for the probe 100 using a microprocessor and optionally a proportional control device, such as a foot pedal or trigger. The microprocessor activates the actuating assembly 160, which actuates the drive shaft 180 so as to move the drive shaft 180, and thus the cutter 130, in a reciprocating fashion along the longitudinal axis of the probe 100 within the needle 120 and/or stiffening sleeve 140 at the desired cut rate. As the cutter 130 moves in a reciprocating fashion within the needle 120, the blade 300 and the aperture 210 interact to cut ocular tissue. The cut ocular tissue and/or fluid is aspirated through the lumen 260 of the cutter 130 to travel through the body 110 toward a collection chamber. As the aspirated tissue and/or fluid travels from the distal portion 290 into the proximal portion 270 of the cutter 130, the rate of flow increases in proportion to the difference in diameters D5 and D4 of the cutter 130.

Unlike conventional vitrectomy probes, which have cutters with constant and uniform diameters, the embodiment of the ophthalmic surgical probe 100 of the present disclosure pictured in FIGS. 1, 2, and 3 includes the aspiration system 145 that expands from a smaller diameter D3 at the distal portion 240 of the needle 120 to a larger diameter D1 at the proximal portion 310 of the stiffening sleeve 140. Within the aspiration system 145, the cutter 130 expands from a smaller diameter D5 at its distal portion 290 to a larger diameter D4 at its proximal portion 270. This proximal expansion of the cutter 130 facilitates decreased flow resistance through the proximal portion 270 of the cutter 130, thus increasing the flow rate through the probe 100. The corresponding proximal expansion of the needle 120 and the stiffening sleeve 140 further contribute to the increased flow rate of the probe 100.

As shown in FIG. 3, the distal portions 240, 290 of the needle 120 and the cutter 130, respectively, which have smaller diameters D3 and D5, respectively, are inserted through the cannula 380 into the eye 370. The cutter 130 widens into the proximal portion 270 proximal of the probe-cannula interface 390, thereby preserving a large gauge (i.e, small diameter) insertion into the cannula 380 and the eye 370 while allowing for improved aspiration through the lumen 260. Increasing the diameter of the aspiration system 145 proximal of the probe-cannula interface 390 decreases the flow resistance through the lumen 260 and thus increases the aspiration flow rate through the probe 100 without increasing trauma to the eye 370 or affecting access into the eye 370. Because the diameter D4 of the proximal portion 270 of the cutter 130 is wider than the diameter D3 of the distal portion 240 of the needle 120, the proximal portion of the cutter 130 is prevented from entering the distal portion 240 of the needle 120. Therefore, this embodiment of the probe 100 provides an enhanced vitrectomy probe that allows adequate stiffness, reduced flow resistance, and an increased flow rate while maintaining a less invasive, large gauge diameter needle and cutter.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An ophthalmic surgical probe for insertion into an eye of a patient, comprising:
    a handpiece body;
    a hollow cutter, the cutter including a first portion having a first outer diameter and a second portion having a second outer diameter sized smaller than the first outer diameter, wherein the first portion and the second portion are in fluid communication;
    a needle including a third transition portion having a third inner diameter and a fourth portion having a fourth inner diameter sized smaller than the third inner diameter, wherein the third transition portion and the fourth portion are in fluid communication and wherein the fourth portion is the distal most portion of the needle and wherein the second portion of the hollow cutter is circumscribed by the fourth portion and the second outer diameter approximates to the fourth inner diameter to allow the hollow cutter to cut tissue as it slides by a port in the fourth portion; and
    a hollow, tubular stiffening sleeve including a fifth portion having a fifth inner diameter and a sixth portion having a sixth inner diameter sized smaller than the fifth inner diameter, wherein the sixth inner diameter approximates to an outer diameter of the fourth portion of the needle, and wherein the third, fourth, fifth, and sixth portions are in fluid communication,
    wherein the cutter is slidably disposed within the needle and the stiffening sleeve and wherein the cutter is coupled to the handpiece body such that a cone-shaped transition section, comprising at least part of the first portion and at least part of the second portion, is configured to move, during cutter operation, inside the hollow stiffening sleeve but not into the handpiece body and not into the fourth portion.

2. The ophthalmic surgical probe of claim 1 wherein the stiffening sleeve comprises a semi-rigid sheath disposed circumferentially around the third portion of the needle and the first portion of the cutter.

3. The ophthalmic surgical probe of claim 1 wherein the first and third portions are located proximal to the eye during and after insertion.

4. The ophthalmic surgical probe of claim 1 further comprising a first connecting portion disposed between the first portion and the second portion such that the first portion, the second portion, and the first connecting portion are in fluid communication.

5. The ophthalmic surgical probe of claim 4 wherein the diameter of the first connecting portion gradually transitions from the first diameter to the second diameter.

6. The ophthalmic surgical probe of claim 1 including a second connecting portion disposed between the fifth portion and the sixth portion such that the fifth portion, the sixth portion, and the second connecting portion are in fluid communication.

7. The ophthalmic surgical probe of claim 6 wherein the diameter of the second connecting portion gradually transitions from the fifth diameter to the sixth diameter.

8. The ophthalmic surgical probe of claim 1 wherein the first portion is slidably disposed within the fifth portion, and wherein the second portion is slidably disposed within the fourth portion.

9. The ophthalmic surgical probe of claim 1, wherein the stiffening sleeve is a cylindrical tube that supports and stabilizes the needle.

10. The ophthalmic surgical probe of claim 1, wherein the stiffening sleeve comprises a cone shaped transition section between the fifth portion and the sixth portion and wherein the needle comprises a cone shaped transition section between the third portion and the fourth portion and wherein the cone shaped transition section of the stiffening sleeve engages the cone shaped transition section of the needle.

11. The ophthalmic surgical probe of claim 1, wherein the stiffening sleeve is a steel tube.

12. The ophthalmic surgical probe of claim 1, wherein the stiffening sleeve, the needle, and the cutter are cylindrical, coaxial, hollow tubes.

13. The ophthalmic surgical probe of claim 1, wherein the stiffening sleeve, the needle, and the cutter are cylindrical, coaxial, thin-walled tubes.

14. The ophthalmic surgical probe of claim 1, wherein the cutter has fewer than three changes of internal diameter.

15. The ophthalmic surgical probe of claim 1, wherein the handpiece body comprises an enlarged outer diameter configured to be held by a surgeon and wherein the stiffening sleeve extends partially into and partially out of the handpiece body.

* * * * *